United States Patent [19]

Doya et al.

[11] Patent Number: 5,489,702
[45] Date of Patent: Feb. 6, 1996

[54] PROCESS FOR THE PRODUCTION OF DIALKYL CARBONATE

[75] Inventors: Masaharu Doya; Ken-ichi Kimizuka; Yutaka Kanbara, all of Niigata, Japan

[73] Assignee: Mitsubishi Gas Chemical Company, Inc., Tokyo, Japan

[21] Appl. No.: 286,203

[22] Filed: Aug. 5, 1994

[30] Foreign Application Priority Data

Aug. 12, 1993 [JP] Japan .................. 5-200852

[51] Int. Cl.⁶ .................. C07C 68/00
[52] U.S. Cl. .................. 558/277
[58] Field of Search .................. 558/277

[56] References Cited

U.S. PATENT DOCUMENTS

| | | | |
|---|---|---|---|
| 4,062,884 | 12/1977 | Romano et al. | 558/277 |
| 4,181,676 | 1/1980 | Buysch et al. | 558/277 X |
| 4,307,032 | 12/1981 | Krimm et al. | 558/277 |
| 4,327,035 | 4/1982 | Heitz et al. | 558/277 X |
| 5,003,084 | 3/1991 | Su et al. | 549/230 |
| 5,214,182 | 5/1993 | Knifton | 558/277 |
| 5,349,077 | 9/1994 | Doya et al. | 558/260 |

FOREIGN PATENT DOCUMENTS

| | | |
|---|---|---|
| 0443758 | 8/1991 | European Pat. Off. . |
| 0581131 | 2/1994 | European Pat. Off. . |
| 2740242 | 3/1979 | Germany . |

*Primary Examiner*—Johann Richter
*Assistant Examiner*—Michael G. Ambrose
*Attorney, Agent, or Firm*—Wenderoth, Lind & Ponack

[57] ABSTRACT

A process for the production of a dialkyl carbonate comprising a first step of reacting an alkylene glycol, or an alkanediol, with urea in the presence of a catalyst to form an alkylene carbonate or a six-membered cyclic carbonate, and a second step of reacting the alkylene carbonate or the six-membered cyclic carbonate with an alcohol in the presence of a catalyst to obtain a dialkyl carbonate and an alkylene glycol, or a dialkyl carbonate and an alkanediol, wherein the alkylene glycol or the alkanediol obtained in the second step is recycled to the first step.

10 Claims, No Drawings

PROCESS FOR THE PRODUCTION OF DIALKYL CARBONATE

FIELD OF THE INVENTION

The present invention relates to a process for the production of a dialkyl carbonate. More specifically, it relates to a process for the production of a dialkyl carbonate from urea and an alcohol in the presence of an alkylene glycol or an alkane diol which is recyclable. The alkyl carbonate is an important compound as a solvent for a resin and a coating composition, an alkylating agent or a carbonylating agent. Further, the alkyl carbonate is useful as an organic solvent, an agent for processing a synthetic fiber, a raw material for a synthetic resin and a drug, or an organic synthesis reagent.

PRIOR ART OF THE INVENTION

The dialkyl carbonate is industrially produced from phosgene as a raw material. However, the high toxicity of phosgene has been recently recognized as a serious problem concerning environmental protection. For avoiding the use of the phosgene, U.S. Pat. No. 5,162,563, JP-A-56-164145 and JP-A-2-19347 disclose a method in which methanol is oxidized and carbonylated, and U.S. Pat. No. 4,307,032 discloses a method in which alkylene carbonate and an alcohol are ester-exchanged.

U.S. Pat. No. 2,773,881 discloses a process for producing alkylene carbonate, in which ethylene oxide and carbon dioxide are allowed to react continuously in the presence of a pyridine catalyst at 240° C. under about 140 atmospheric pressures. The problem with this process is that the temperature and pressure are high and that ethylene oxide has a high risk of explosion.

European Patent 443,758 discloses a process for producing alkylene carbonate from glycol and urea under atmospheric pressure or elevated pressure in the absence of a catalyst or in the presence of a tin compound as a catalyst. In this process, the selectivity to alkylene carbonate on the basis of glycol which has reacted is as high as 84 to 99%. However, the conversion of glycol is 66% of the theoretical value or less, and the selectivity to alkylene carbonate on the basis of urea is as low as 63% or less. The amount of urea which is decomposed is large.

As a process for producing a six-membered carbonate, DE-310313741 discloses a process for producing a cyclic carbonate from alkanediol and urea in the presence of an ester-exchange catalyst. This process cannot be said to be industrially advantageous, since the yields are as low as about 80% and the reaction time is as long as 10 to 20 hours.

As described above, as a substitute for the method using phosgene, there have been proposed a process in which methanol is oxidized and carbonylated, and a process in which alkylene carbonate and alcohol are ester-exchanged.

With regard to the process in which methanol is oxidized and carbonylated, there have been proposed a gaseous phase method in which methanol and nitrous acid ester are allowed to react in a gaseous phase (U.S. Pat. No. 5,162,563) and a liquid phase method in which they are allowed to react in a liquid phase (JP-A-2-19347). The former method has a problem in the use of a corrosive gas (nitrous acid ester), and the latter method has a problem in that the reaction pressure is high, that the catalyst is expensive and that the nitrous acid ester is corrosive.

In the process in which alkylene carbonate and alcohol are ester-exchanged, alkylene carbonate and alcohol easily react with each other since the reaction is an equilibrium reaction, while the alkylene carbonate as a raw material is expensive, and alkylene glycol is formed as a byproduct.

SUMMARY OF THE INVENTION

It is an object of the present invention to provide an industrially advantageous process for the production of a dialkyl carbonate from inexpensive raw materials by a safe method.

It is another object of the present invention to provide a process for the production of a dialkyl carbonate, which process uses no corrosive gas and which can utilize alkylene glycol or alkanediol produced as a byproduct.

It is further another object of the present invention to provide a process for the production of a dialkyl carbonate from urea and an alcohol as substantial raw materials.

According to the present invention, there is provided a process for the production of a dialkyl carbonate, which comprises a first step of reacting an alkylene glycol of the formula (1),

$$R^1CH(OH)CH(OH)R^2 \qquad (1)$$

wherein each of $R^1$ and $R^2$ is independently a hydrogen atom or an alkyl group having 1 to 4 carbon atoms, or an alkanediol of the formula (2),

$$R^3CH(OH)-\underset{\underset{R^5}{|}}{\overset{\overset{R^4}{|}}{C}}-CH(OH)R^6 \qquad (2)$$

wherein each of $R^3$ to $R^6$ is independently a hydrogen atom or an alkyl group having 1 to 4 carbon atoms, with urea to form an alkylene carbonate derived from the alkylene glycol of the formula (1) or a six-membered cyclic carbonate derived from the alkanediol of the formula (2), and a second step of reacting the alkylene carbonate or the six-membered cyclic carbonate with an alcohol to obtain a dialkyl carbonate and an alkylene glycol, or a dialkyl carbonate and an alkanediol, wherein: the alkylene glycol or the alkanediol obtained in the second step is recycled to the first step.

DETAILED DESCRIPTION OF THE INVENTION

The present inventors have made diligent studies to achieve the above objects, and as a result have found the following (the invention (1)): A dialkyl carbonate can be industrially advantageously produced from easily available urea and an alcohol by reacting urea and alkylene glycol to form a five-membered cyclic alkylene carbonate in a first step, reacting the alkylene carbonate and an alcohol to form a dialkyl carbonate in a second step, and recycling alkylene glycol formed as a byproduct to the first step.

The present inventors have also found the following (the invention (2)): A dialkyl carbonate can be industrially advantageously produced from easily available urea and an alcohol by reacting urea and a specific alkanediol to form a six-membered cyclic carbonate in a fist step, and reacting the six-membered cyclic carbonate and an alcohol, and in this case, a specific alkanediol formed as a byproduct can be recycled to the first step.

A zinc-, magnesium-, lead- or calcium-based catalyst is suitable for use in the reaction between either the alkylene glycol or alkanediol and urea in the first step. Particularly, this reaction is preferably carried out under reduced pressure, since the alkylene carbonate or six-membered cyclic carbonate can be obtained at high yields. The catalyst which is used in the first step and remains in the reaction mixture still retains its activity in the ester-exchange reaction carried out in the second step. Therefore, the reaction mixture containing the catalyst in the first step may be directly used in the second step. Further, unreacted alkylene glycol or unreacted alkanediol may be removed from the reaction mixture containing the catalyst in the first step, and the remainder containing the catalyst may be used in the second step.

The alkylene glycol or the alkanediol recovered from the reaction mixture produced in the second step is recycled to the first step. The unreacted alkylene carbonate or unreacted six-membered cyclic carbonate containing the catalyst, recovered from the reaction mixture formed in the second step, is recycled to the reaction system in the second step. In this case, it is preferred to separate part of the catalyst from the unreacted alkylene carbonate or unreacted six-membered cyclic carbonate containing the catalyst, and to use the separated catalyst in the first step. When the catalyst used in the first step is the same as the catalyst used in the second step, the catalyst used in the first step may be used in the second step, and the catalyst used in the second step may be recycled to the first step.

In the present invention, the alkylene glycol, the alkanediol and the catalyst can be recycled, i.e., can be used in a circulating manner. Therefore, a dialkyl carbonate can be substantially produced from urea and an alcohol. That is, the characteristic feature of the present invention is that a dialkyl carbonate can be easily produced from relatively inexpensive raw materials at high yields.

In the present invention (1), the first and second steps are shown by the following reaction scheme.

(First step)

(Second step)

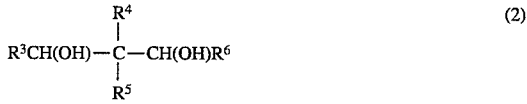

In the above reaction scheme, each of $R^1$ and $R^2$ is independently a hydrogen atom or an alkyl group having 1 to 4 carbon atoms, and R' is an alkyl or alicyclic group.

In the present invention (2), the first and second steps are shown by the following reaction scheme.

(First step)

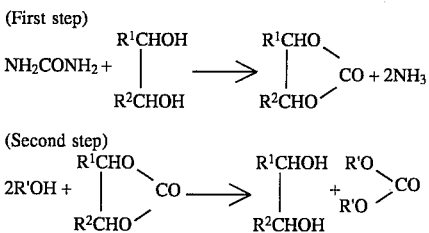

(Second step)

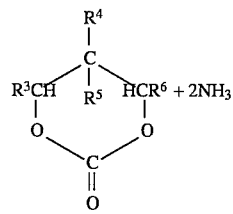

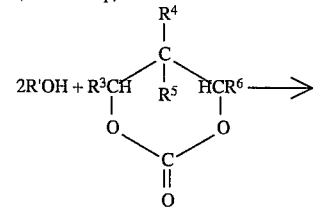

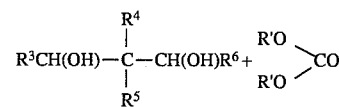

In the above reaction scheme, each of $R^3$ to $R^6$ is independently a hydrogen atom or an alkyl group having 1 to 4 carbon atoms, and R' is an alkyl or alicyclic group.

In the present invention, the first step for producing an alkylene carbonate or a six-membered cyclic carbonate from urea and either alkylene glycol or alkanediol is generally carried out by adding a catalyst to a solution mixture of urea with alkylene glycol or alkanediol and heating the resultant mixture.

The alkylene glycol used as a raw material in the fist step refers to a compound of the formula (1), $$R^1CH(OH)CH(OH)R^2 \qquad (1)$$

wherein each of $R^1$ and $R^2$ is independently a hydrogen atom or an alkyl group having 1 to 4 carbon atoms.

The alkanediol used as a raw material in the first step refers to a compound of the formula (2),

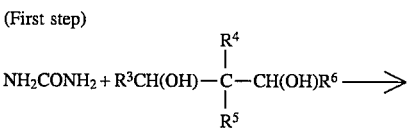

wherein each of $R^3$ to $R^6$ is independently a hydrogen atom or an alkyl group having 1 to 4 carbon atoms.

The above alkylene glycol includes ethylene glycol, 1,2-propylene glycol and 1,2-butylene glycol.

The above alkanediol includes 1,3-propanedial, 1,3-butanedial, 1,3-pentanediol, 2,4-pentanediol, 1,4-hexanediol, 2,4-hexanediol, 2-methyl-2,4-pentanediol and neopentyl glycol.

The amount of the alkylene glycol or the alkanediol per mole of urea is required to be at least 1 mol. When the molar ratio of the alkylene glycol or the alkanediol to urea is 1.1 to 1.5, advantageously, the reaction mixture containing the catalyst, obtained in the first step, can be directly fed to the second step. When the molar ratio of the alkylene glycol or the alkanediol to urea is less than 1, the selectivity to the alkylene carbonate or the six-membered cyclic carbonate decreases due to a side reaction of the urea.

In the present invention, the catalyst used in the first step includes metals such as zinc, magnesium, lead and calcium and compounds of these metals.

The above catalyst is generally selected from powders, oxides, suboxides, hydroxides, inorganic salts, carbonates, basic carbonates, organic salts and organic compounds of metals such as zinc, magnesium, lead and calcium. Further, as a catalyst, there may be used reaction products from the reactions of the above metal compounds with organic compounds present in the reaction system such as urea, alkylene glycol, alkanediol, alkylene carbonate, six-membered cyclic carbonate, alcohol and dialkyl carbonate.

The above compounds (catalysts) may be used alone or in combination. Further, the above catalyst may be used as a mixture thereof with a compound inert to the reaction or one supported by a carrier inert to the reaction.

The amount of the catalyst is not specially limited, while the catalyst is used in such an amount that the amount of zinc, magnesium, lead or calcium per mole of urea is 0.0001 to 10 mol, preferably 0.001 to 1 mol.

In the first step of the present invention, an excess amount of the alkylene glycol or the alkanediol is used for increasing the selectivity to the alkylene carbonate or the six-membered cyclic carbonate, and it is hence not necessarily required to use a solvent. When the raw material has a high boiling point, a high melting point or a high viscosity, it is preferred to use a solvent.

The solvent is not specially limited if it is inert to the reaction and can be dissolved in the reaction system. The solvent is preferably selected from cyclic carbonate, an aromatic hydrocarbon and an ether.

Although not specially limited, the amount of the solvent per mole of urea is generally 0.1 to 10 mol.

In the present invention, the first step is carried out by maintaining a mixture of urea, either the alkylene glycol or the alkanediol and the catalyst at a reaction temperature while removing formed ammonia from the reaction system.

For removing ammonia, inert gas may be introduced into the reaction mixture under reaction conditions. The inert gas is generally selected from nitrogen and carbon dioxide. The amount of the inert gas per mole of ammonia is 1 to 100 mol. Further, in place of the inert gas, more effectively, the reaction in the first step is performed under the reflux of the alkylene glycol, the alkanediol, or the solvent. The amount of the alkylene glycol, the alkanediol or the solvent under reflux is 1 to 100 mol per mole of the ammonia.

In the present invention, the reaction temperature in the first step is properly 120° to 200° C. When the reaction temperature is too low, the reaction rate is low. When it is too high, the amount of byproducts increases.

The reaction pressure may be atmospheric pressure or elevated pressure, For easily removing ammonia, the reaction is preferably carried out under reduced pressure. The reduced pressure is in the range of from 5 to 700 mmHg, and the reduced pressure is properly selected so that the alkylene glycol, the alkanediol or the solvent is refluxed at a reaction temperature.

The reaction time differs depending upon the alkylene glycol or the alkanediol, the molar ratio of the alkylene glycol or the alkanediol to urea, the catalyst, the amount of the catalyst, the reaction temperature and the amount of the alkylene glycol, the alkanediol or the solvent, while the reaction time is generally 0.5 to 10 hours.

In the second step, either the alkylene carbonate or the six-membered cyclic carbonate and an alcohol are ester-exchanged to form a dialkyl carbonate, and the reaction for this ester-exchange is generally carried out by adding a catalyst to a mixture of either the alkylene carbonate or the six-membered cyclic carbonate with an alcohol and heating the resultant mixture.

The alkylene carbonate or the six-membered cyclic carbonate formed in the first step can be easily isolated from the reaction mixture by a conventional method such as distillation, and used in the second step.

When the above catalyst, i.e., a zinc, magnesium, lead or calcium catalyst, used in the first step is used in the second step, this catalyst still has the activity for the ester-exchange reaction in the second step. It is therefore industrially advantageous to use the reaction mixture containing the catalyst, obtained in the first step, as a raw material for the second step as it is or after unreacted alkylene glycol or unreacted alkanediol and the solvent are removed by distillation, since the process is so simplified.

In the ester-exchange reaction in the second step, the alcohol as a raw material is selected from aliphatic alcohols having 1 to 6 carbon atoms, preferably 1 to 4 carbon atoms, such as methyl alcohol, ethyl alcohol, propyl alcohol and isopropyl alcohol and alicyclic alcohols such as cyclohexanol.

Although not specially limited, the amount of the alcohol per mole of the alkylene carbonate or the six-membered cyclic carbonate is 1 to 20 mol.

In the present invention, the catalyst used in the second step is not specially limited, while it is economical and processwise advantageous to use the catalyst used in the first step. When the same catalyst is used in the first step and the second step, the reaction mixture containing the catalyst, obtained in the first step, is used for the reaction in the second step, and the alkanediol or the alkylene glycol and the solvent, recovered from the reaction mixture obtained in the second step can be recycled to the first step.

The reaction temperature in the second step is 60° to 200° C. When the reaction temperature is too low, the reaction rate is low and the selectivity to the dialkyl carbonate (from six-membered cyclic carbonate) is low. When it is too high, the amount of byproducts increases.

The reaction time differs depending upon the alcohol and the alkylene carbonate or the six-membered cyclic carbonate as raw materials, the amount ratio of these, the catalyst and the amount of the catalyst, while the reaction time is generally 0.1 to 10 hours.

The reaction pressure in the second step may be a pressure under which the reaction is carried out in a liquid phase, while it is generally in the range of from 0 to 20 kg/cm².

In the second step of the present invention (2), generally, alkyl-3-hydroxyalkyl carbonate is formed in addition to the dialkyl carbonate. This alkyl-3-hydroxyalkyl carbonate is an intermediate between the six-membered cyclic carbonate and the dialkyl carbonate. After the alcohol and the dialkyl carbonate are separated from the reaction mixture obtained in the second step, the above intermediate and the unreacted six-membered cyclic carbonate are re-cycled in the second step, whereby the yield of the dialkyl carbonate increases.

After the reaction in the second step, the dialkyl carbonate formed in the second step can be recovered by easily separating it from the reaction mixture by a conventional method such as distillation.

In the second step in the present invention (1), formed dialkyl carbonate, unreacted alcohol and formed alkylene glycol are separated from the reaction mixture by distillation. The separated alkylene glycol is recycled to the first step. The remaining reaction mixture (from which the formed dialkyl carbonate, the unreacted alcohol and the formed alkylene glycol have been separated) is separated into unreacted alkylene carbonate and the catalyst. The separated, unreacted alkylene carbonate can be used in the second step, and the separated catalyst can be used in any one of the first and second steps. Further, part of the catalyst may be separated from the above remaining reaction mixture and recycled to the first step, and the remainder (alkylene carbonate containing a remaining catalyst) can be used in the second step. For recycling the catalyst used and recovered in the second step to the first step, it is preferred to use the same catalyst in the first and second steps.

In the second step in the present invention (2), formed dialkyl carbonate, unreacted alcohol and formed alkanediol are separated from the reaction mixture by distillation. The separated alkanediol is recycled to the first step. The remaining reaction mixture (from which the formed dialkyl carbonate, the unreacted alcohol and the formed alkanediol have been separated) is separated into unreacted six-membered cyclic carbonate and the catalyst. The unreacted six-membered cyclic carbonate can be used in the second step, and the catalyst can be used in any one of the first and second steps. Further, part of the catalyst may be separated from the above remaining reaction mixture and recycled to the first step. For recycling the catalyst used and recovered in the second step to the first step, it is preferred to use the same catalyst in the first and second steps.

In the second step in the present invention (2), generally, alkyl-3-hydroxyalkyl carbonate is formed in addition to the dialkyl carbonate as described already. In this case, the alkyl-3-hydroxyalkyl carbonate can be recycled to the reaction system in the second step together with part of the unreacted six-membered cyclic carbonate.

The process of the present invention can be carried out by any one of a batch method and a continuous method.

As detailed above, the present invention provides a process for the production of dialkyl carbonate, in which alkylene carbonate or six-membered cyclic carbonate can be produced from urea and either alkylene glycol or alkanediol at high yields in the first step and alkylene glycol or alkanediol produced as a byproduct in the second step can be recycled to the first step. In the process of the present invention, dialkyl carbonate can be produced substantially from urea and an alcohol. In the process of the present invention, dialkyl carbonate can be produced from easily available inexpensive materials at high yields.

In the process of the present invention, the same catalyst can be used both in the first step of producing alkylene carbonate or six-membered cyclic carbonate and in the second step of producing dialkyl carbonate by an ester-exchange reaction. In the process of the present invention, the process for the production of dialkyl carbonate can be remarkably simplified, and recovered catalyst and remaining reaction mixture can be recycled.

Further, in the process of the present invention, dialkyl carbonate can be produced in the absence of toxic gas or explosive gas, by a liquid phase reaction at a highly safe, low pressure.

The present invention will be detailed hereinafter with reference to Examples. However, the present invention shall not be limited to these Examples.

In the Examples, the conversion of glycol is calculated by the following equation. The amount of unreacted glycol is obtained by measuring a reaction mixture, and the amount of glycol entailed by formed ammonia is included in a reaction amount (amount of glycol–amount of unreacted glycol). The conversion of glycol therefore sometimes shows a value exceeding a theoretical value. Similarly, the conversion of alkanediol sometimes shows a value exceeding a theoretical value.

Conversion of glycol (%)=(Amount of fed glycol–amount of unreacted glycol)/amount of fed glycol×100

The conversion of alkanediol is also calculated as follows.

Conversion of alkanediol (%)=(Amount of fed alkanediol–amount of unreacted alkanediol)/amount of fed alkanediol×100.

EXAMPLE 1

(First step)

A 300-ml three-necked flask equipped with a Snyder's fractionating column having a reflux condenser in an upper portion and a thermometer was charged with 60.1 g (1.00 mol) of urea, 77.6 g (1.25 mol) of ethylene glycol and 3 g of zinc oxide, and while the mixture was stirred, the pressure in the flask was reduced to 100 mmHg and the mixture was heated to 145° C. The mixture was allowed to react for 2 hours, and then the reaction mixture was cooled. The amount of the reaction mixture was 106.1 g. The reaction mixture was analyzed for a composition by gas chromatography to show 15.4 g of unreacted ethylene glycol and 86.0 g of formed ethylene carbonate.

The above results show the following. The conversion of ethylene glycol is 80.1% under the theoretical value of 80.0%, the selectivity to ethylene carbonate on the basis of the reacted ethylene glycol is 97.5%, and the selectivity to ethylene carbonate on the basis of urea is 97.6% (conversion of urea=100%).

(Second step)

A 300-ml autoclave was charged with the entire amount of the reaction mixture obtained in the first step and 64.1 g (2.0 mol) of methanol and flushed with nitrogen. Then, the mixture was heated up to 140° C. with stirring. The mixture was allowed to react for 1 hour, and the reaction mixture was cooled and analyzed for a composition by gas chromatography to show 44.8 g of methanol, 27.0 g of dimethyl carbonate, 34.1 g of ethylene glycol and 59.3 g of ethylene carbonate.

The above results show the following. The conversion of ethylene carbonate is 31.0%, and the selectivity to dimethyl carbonate on the basis of the reacted ethylene carbonate is at least 99%.

EXAMPLE 2

(First step)

The first step of Example 1 was repeated except that the zinc oxide as a catalyst was replaced with magnesium oxide, to give 104.5 g of a reaction mixture. The reaction mixture was analyzed for a composition by gas chromatography to show 16.1 g of unreacted ethylene glycol and 83.9 g of formed ethylene carbonate.

The above results show the following. The conversion of glycol is 79.2% under the theoretical value of 80.0%, the selectivity to ethylene carbonate on the basis of the reacted ethylene glycol is 96.2%, and the selectivity to ethylene carbonate on the basis of urea is 95.2% (conversion of urea=100%).

(Second step)

A 300-ml autoclave was charged with the entire amount of the reaction mixture obtained in the first step and 64.1 g (2.0 mol) of methanol and flushed with nitrogen. Then, the mixture was heated up to 120° C. with stirring. The mixture was allowed to react for 1 hour, and the reaction mixture was cooled and analyzed for a composition by gas chromatography to show 44.9 g of methanol, 26.9 g of dimethyl carbonate, 34.6 g of ethylene glycol and 57.4 g of ethylene carbonate.

The above results show the following. The conversion of ethylene carbonate is 31.5%, and the selectivity to dimethyl carbonate on the basis of the reacted ethylene carbonate is at least 99%.

EXAMPLE 3

(First step)

The first step of Example 1 was repeated except that the zinc oxide as a catalyst was replaced with lead oxide and that the reaction time was changed from 2 hours to 4 hours, to give 103.8 g of a reaction mixture. The reaction mixture was analyzed for a composition by gas chromatography to show 16.7 g of unreacted ethylene glycol and 83.6 g of formed ethylene carbonate.

The above results show the following. The conversion of glycol is 78.5% under the theoretical value of 80.0%, the selectivity to ethylene carbonate on the basis of the reacted ethylene glycol is 96.8%, and the selectivity to ethylene carbonate on the basis of urea is 95.0% (conversion of urea=100%).

(Second step)

A 300-ml autoclave was charged with the entire amount of the reaction mixture obtained in the first step and 64.1 g (2.0 mol) of methanol and flushed with nitrogen. Then, the mixture was heated up to 120° C. with stirring. The mixture was allowed to react for 1 hour, and the reaction mixture was cooled and analyzed for a composition by gas chromatography to show 45.9 g of methanol, 25.6 g of dimethyl carbonate, 34.3 g of ethylene glycol and 58.5 g of ethylene carbonate.

The above results show the following. The conversion of ethylene carbonate is 30.1%, and the selectivity to dimethyl carbonate on the basis of the reacted ethylene carbonate is at least 99%.

EXAMPLE 4

(First step)

The first step of Example 1 was repeated except that the zinc oxide as a catalyst was replaced with 1.5 g of calcium oxide, that the pressure was changed to 80 mmHg, that the reaction temperature was changed to 135° C. and that the reaction time was changed from 2 hours to 6 hours, to give 102.1 g of a reaction mixture. The reaction mixture was analyzed for a composition by gas chromatography to show 15.3 g of unreacted ethylene glycol and 84.1 g of formed ethylene carbonate.

The above results show the following. The conversion of glycol is 80.3% under the theoretical value of 80.0%, the selectivity to ethylene carbonate on the basis of the reacted ethylene glycol is 95.1%, and the selectivity to ethylene carbonate on the basis of urea is 95.4% (conversion of urea=100% ).

(Second step)

A 300-ml autoclave was charged with the entire amount of the reaction mixture obtained in the first step and 64.1 g (2.0 mol) of methanol and flushed with nitrogen. Then, the mixture was heated up to 60° C. with stirring. The mixture was allowed to react for 1 hour, and the reaction mixture was cooled and analyzed for a composition by gas chromatography to show 44.4 g of methanol, 27.5 g of dimethyl carbonate, 34.2 g of ethylene glycol and 56.9 g of ethylene carbonate.

The above results show the following. The conversion of ethylene carbonate is 32.3%, and the selectivity to dimethyl carbonate on the basis of the reacted ethylene carbonate is at least 99%.

EXAMPLE 5

(First step)

The same reactor as that used in Example 1 was charged with 60.1 g (1.00 mol) of urea, 95.1 g (1.25 mol) of propylene glycol and 1.5 g of zinc oxide, and while the mixture was stirred, the pressure in the reactor was reduced to 280 mmHg and the mixture was heated to 170° C. The mixture was allowed to react for 1.5 hours, and then the reaction mixture was cooled. The amount of the reaction mixture was 122.2 g. The reaction mixture was analyzed for a composition by gas chromatography to show 18.8 g of unreacted propylene glycol and 101.2 g of formed propylene carbonate.

The above results show the following. The conversion of glycol is 80.2% under the theoretical value of 80.0%, the selectivity to propylene carbonate on the basis of the reacted propylene glycol is 98.9%, and the selectivity to propylene carbonate on the basis of urea is 99.1% (conversion of urea=100%).

(Second step)

A 300-ml autoclave was charged with the entire amount of the reaction mixture obtained in the first step and 64.1 g (2.0 mol) of methanol and flushed with nitrogen. Then, the mixture was heated up to 140° C. with stirring. The mixture was allowed to react for 1 hour, and the reaction mixture was cooled and analyzed for a composition by gas chromatography to show 52.0 g of methanol, 16.9 g of dimethyl carbonate, 33.2 g of propylene glycol and 81.9 g of propylene carbonate.

The above results show the following. The conversion of propylene carbonate is 19.0%, and the selectivity to dimethyl carbonate on the basis of the reacted propylene carbonate is at least 99%.

EXAMPLE 6

(First step)

A reaction mixture was obtained in the same manner as in the first step of Example 5.

(Second step)

A 300-ml autoclave was charged with the entire amount of the reaction mixture obtained in the first step and 92.1 g (2.0 mol) of ethanol and flushed with nitrogen. Then, the mixture was heated up to 140° C. with stirring. The mixture was allowed to react for 1 hour, and the reaction mixture was cooled and analyzed for a composition by gas chromatography to show 76.2 g of ethanol, 20.3 g of diethyl carbonate, 32.0 g of propylene glycol and 83.5 g of propylene carbonate.

The above results show the following. The conversion of propylene carbonate is 17.4%, and the selectivity to diethyl carbonate on the basis of the reacted propylene carbonate is at least 99%.

EXAMPLE 7

(First step)

The same reaction mixture as that obtained in the second step of Example 5 was concentrated by distillation to prepare 2.2 g of a high boiling product having a high boiling point and containing the catalyst.

The first step of Example 5 was repeated except that the catalyst was replaced with the above high boiling product, to give 123.0 g of a reaction mixture. The reaction mixture was analyzed for a composition by gas chromatography to show 19.1 g of unreacted propylene glycol and 101.5 g of formed propylene carbonate.

The above results show the following. The conversion of propylene glycol is 79.9% under the theoretical value of 80.0%, the selectivity to propylene carbonate on the basis of the reacted propylene glycol is 99.5%, and the selectivity to propylene carbonate on the basis of urea is 99.4% (conversion of urea=100%).
(Second step)

A 300-ml autoclave was charged with the entire amount of the reaction mixture obtained in the first step and 64.1 g (2.0 mol) of methanol and flushed with nitrogen. Then, the mixture was heated up to 140° C. with stirring. The mixture was allowed to react for 1 hour, and the reaction mixture was cooled and analyzed for a composition by gas chromatography to show 50.7 g of methanol, 18.8 g of dimethyl carbonate, 34.9 g of propylene glycol and 80.2 g of propylene carbonate.

The above results show the following. The conversion of propylene carbonate is 21.0%, and the selectivity to dimethyl carbonate on the basis of the reacted propylene carbonate is at least 99%.

EXAMPLE 8

(First step)

A 300-ml three-necked flask equipped with a Snyder's fractionating column having a reflux condenser in an upper portion, a stirrer and a thermometer was charged with 60.1 g (1.0 mol) of urea, 108.1 g (1.2 mol) of 1,3-butanedial and 8.0 g of zinc acetate, and while the mixture was stirred, the pressure in the flask was reduced to 50 mmHg and the mixture was heated to 155° C. The mixture was allowed to react for 5 hours, and then the reaction mixture was cooled. The amount of the reaction mixture was 143.1 g. The reaction mixture was analyzed for a composition by gas chromatography to show 23.5 g of unreacted 1,3-butanedial and 103.1 g of formed 1,3-dioxane-4-methyl-2-one.

The above results show the following. The conversion of 1,3-butanedial is 78.2% under the theoretical value of 83.3%, the selectivity to 1,3-dioxane-4-methyl-2-one on the basis of 1,3-butanedial is 94.6%, and the yield of 1,3-dioxane-4-methyl-2-one on the basis of urea is 88.8% (conversion of urea=100%).
(Second step)

A 500-ml autoclave having a thermometer was charged with the entire amount of the reaction mixture obtained in the first step and 64.1 g (2.0 mol) of methanol and flushed with nitrogen. Then, the mixture was heated to 120° C. with stirring. The mixture was allowed to react for 3 hours, and the reaction mixture was cooled and analyzed for a composition by gas chromatography to show 52.6 g of unreacted 1,3-dioxane-4-methyl-2-one, 40.1 g of methanol, 28.8 g of formed dimethyl carbonate and 16.3 g of methyl-3-hydroxybutyl carbonate.

The above results show the following. The conversion of 1,3-dioxane-4-methyl-2-one is 49.0%, and on the basis of the reacted 1,3-dioxane-4-methyl-2-one, the selectivity to dimethyl carbonate is 73.4% and the selectivity to methyl-3-hydroxybutyl carbonate is 25.1% (total 98.5%).

EXAMPLE 9

(First step)

A 300-ml three-necked flask equipped with a Snyder's fractionating column having a reflux condenser in an upper portion, a stirrer and a thermometer was charged with 60.1 g (1.00 mol) of urea, 95.1 g (1.25 mol) of 1,3-propanediol and 6.0 g of lead carbonate, and while the mixture was stirred, the pressure in the flask was reduced to 80 mmHg and the mixture was heated to 175° C. The mixture was allowed to react for 5 hours, and then the reaction mixture was cooled. The amount of the reaction mixture was 127.8 g. The reaction mixture was analyzed for a composition by gas chromatography to show 21.0 g of unreacted 1,3-propanediol and 92.1 g of formed 1,3-dioxan-2-one.

The above results show the following. The conversion of 1,3-propanediol is 77.9% under the theoretical value of 80.0%, the selectivity to 1,3-dioxan-2-one on the basis of 1,3-propanediol is 92.6%, and the yield of 1,3-dioxan-2-one on the basis of urea is 90.2% (conversion of urea=100%).
(Second step)

A 500-ml autoclave having a thermometer was charged with the entire amount of the reaction mixture obtained in the first step and 138.2 g (3.0 mol) of ethanol and flushed with nitrogen. Then, the mixture was heated to 150° C. with stirring. The mixture was allowed to react for 1 hour, and the reaction mixture was cooled and analyzed for a composition by gas chromatography to show 42.7 g of unreacted 1,3-dioxan-2-one, 98.1 g of ethanol, 45.6 g of formed diethyl carbonate and 13.7 g of ethyl-3-hydroxypropyl carbonate.

The above results show the following. The conversion of 1,3-dioxan-2-one is 53.6%, and on the basis of the reacted 1,3-dioxan-2-one, the selectivity to diethyl carbonate is 79.9% and the selectivity to ethyl-3-hydroxypropyl carbonate is 19.1% (total 99.0%).

EXAMPLE 10

(First step)

A 500-ml three-necked flask equipped with a Snyder's fractionating column having a reflux condenser in an upper portion, a stirrer and a thermometer was charged with 60.1 g (1.00 mol) of urea, 156.2 g (1.5 mol) of neopentyl glycol, 3.0 g of magnesium carbonate and 102.1 g (1.00 mol) of propylene carbonate, and while the mixture was stirred, the pressure in the flask was reduced to 50 mmHg and the mixture was heated to 185° C. The mixture was allowed to react for 3 hours, and then the reaction mixture was cooled. The amount of the reaction mixture was 286.3 g. The reaction mixture was analyzed for a composition by gas chromatography to show 55.3 g of unreacted neopentyl glycol and 123.0 g of formed 1,3-dioxane-5,5-dimethyl-2-one.

The above results show the following. The conversion of neopentyl glycol is 64.6% under the theoretical value of 66.7%, the selectivity to 1,3-dioxane-5,5-dimethyl-2-one on the basis of neopentyl glycol is 97.5%, and the yield of 1,3-dioxane-5,5-dimethyl-2-one on the basis of urea is 94.5% (conversion of urea=100%).

Unreacted neopentyl glycol and propylene carbonate were drawn from the above reaction mixture by distillation to give 127.4 g of a residue containing the catalyst. This residue was analyzed by gas chromatography to show 121.5 g of 1,3-dioxane-5,5-dimethyl-2-one.
(Second step)

The same autoclave as that used in the second step of Example 9 was charged with the entire amount of the residue containing the catalyst, obtained in the first step, and 240.4 g (4.0 mol) of 1-propanol and flushed with nitrogen. Then, the mixture was heated to 165° C. with stirring. The mixture was allowed to react for 1 hour, and the reaction mixture was cooled and analyzed for a composition by gas chromatography to show 33.8 g of unreacted 5,5-dimethyl-1,3-dioxan-2-one, 165.7 g of 1-propanol, 78.9 g of formed dipropyl carbonate and 23.4 g of propyl-3-hydroxy-2,2-dimethylpropyl carbonate.

The above results show the following. The conversion of 5,5-dimethyl-1,3-dioxan-2-one is 72.2%, and on the basis of the reacted 5,5-dimethyl-1,3-dioxan-2-one, the selectivity to dipropyl carbonate is 80.1% and the selectivity to propyl-3-hydroxy-2,2-dimethylpropyl carbonate is 18.1% (total 98.2%).

EXAMPLE 11

(First step)

A 500-ml three-necked flask equipped with a Snyder's fractionating column having a reflux condenser in an upper portion, a stirrer and a thermometer was charged with 60.1 g (1.00 mol) of urea, 130.2 g (1.25 mol) of neopentyl glycol, 3.0 g of dimethoxyzinc and 120.2 g (1.00 mol) of mesitylene, and while the mixture was stirred, the pressure in the flask was reduced to 600 mmHg and the mixture was heated to 145° C. The mixture was allowed to react for 7 hours, and then the reaction mixture was cooled. The amount of the reaction mixture was 280.5 g. The reaction mixture was analyzed for a composition by gas chromatography to show 27.8 g of unreacted neopentyl glycol and 115.5 g of formed 1,3-dioxane-5,5-dimethyl-2-one.

The above results show the following. The conversion of neopentyl glycol is 78.7% under the theoretical value of 80%, the selectivity to 1,3-dioxane-5,5-dimethyl-2-one on the basis of neopentyl glycol is 90.3 %, and the yield of 1,3-dioxane-5 5-dimethyl-2-one on the basis of urea is 88.8% (conversion of urea=100%).

Unreacted neopentyl glycol and mesitylene were drawn from the above reaction mixture by distillation to give 128.5 g of a residue containing the catalyst. This residue was analyzed by gas chromatography to show 114.3 g of 1,3-dioxane-5,5-dimethyl-2-one.

(Second step)

The same autoclave as that used in the second step of Example 9 was charged with the entire amount of the residue containing the catalyst, obtained in the first step, and 64.1 g (2.0 mol) of methanol and flushed with nitrogen. Then, the mixture was heated to 125° C. with stirring. The mixture was allowed to react for 1 hour, and the reaction mixture was cooled and analyzed for a composition by gas chromatography to show 52.0 g of unreacted 5,5-dimethyl-1,3-dioxan-2-one, 37.4 g of methanol, 32.1 g of formed dimethyl carbonate and 18.6 g of methyl-3-hydroxy-2,2-dimethylpropyl carbonate.

The above results show the following. The conversion of 5,5-dimethyl-1,3-dioxan-2-one is 54.4%, and on the basis of the reacted 5,5-dimethyl-1,3-dioxan-2-one, the selectivity to dimethyl carbonate is 74.3% and the selectivity to methyl-3-hydroxy-2,2-dimethylpropyl carbonate is 24.0% (total 98.3%).

EXAMPLE 12

(First step)

The same reaction mixture as that obtained in the second step of Example 8 was concentrated by distillation to prepare 13.3 g of a high boiling product having a high boiling point and containing the catalyst.

The first step of Example 8 was repeated except that the catalyst was replaced with the above high boiling product, to give 148.7 g of a reaction mixture. The reaction mixture was analyzed for a composition by gas chromatography to show 20.1 g of unreacted 1,3-butanediol and 110.1 g of formed 1,3-dioxane-4-methyl-2-one.

The above results show the following. The conversion of 1,3-butanediol is 81.3 % under the theoretical value of 83.3%, the selectivity to 1,3-dioxane-4-methyl-2-one on the basis of 1,3-butanediol is 97.3%, and the yield of 1,3-dioxane-4-methyl-2-one on the basis of urea is 94.9% (conversion of urea=100%).

(Second step)

A 300-ml autoclave having a thermometer was charged with the entire amount of the reaction mixture obtained in the first step and 64.1 g (2.0 mol) of methanol and flushed with nitrogen. Then, the mixture was heated to 120° C. with stirring. The mixture was allowed to react for 3 hours, and the reaction mixture was cooled and analyzed for a composition by gas chromatography to show 57.2 g of unreacted 1,3-dioxane-4-methyl-2-one, 37.9 g of methanol, 32.4 g of formed dimethyl carbonate and 11.0 g of methyl-3-hydroxybutyl carbonate.

The above results show the to following. The conversion of 1,3-dioxane-4-methyl-2-one is 48.1%, and on the basis of the reacted 1,3-dioxane-4-methyl-2-one, the selectivity to dimethyl carbonate is 78.7% and the selectivity to methyl-3-hydroxybutyl carbonate is 16.1% (total 94.8%).

What is claimed is:

1. A process for the production of a dialkyl carbonate, which comprises a first step of reacting an alkylene glycol of the formula (1), $$R^1CH(OH)CH(OH)R^2 \qquad (1)$$

wherein each of $R^1$ and $R^2$ is independently a hydrogen atom or an alkyl group having 1 to 4 carbon atoms, or an alkanediol of the formula (2), $$R^3CH(OH)-\underset{\underset{R^5}{|}}{\overset{\overset{R^4}{|}}{C}}-CH(OH)R^6 \qquad (2)$$

wherein each of $R^3$ to $R^6$ is independently a hydrogen atom or an alkyl group having 1 to 4 carbon atoms, with urea in the presence of a catalyst to form an alkylene carbonate derived from the alkylene glycol of the formula (1) or six-membered cyclic carbonate derived from the alkanediol of the formula (2), and a second step of reacting the alkylene carbonate or the six-membered cyclic carbonate with an alcohol in the presence of a catalyst to obtain a dialkyl carbonate and an alkylene glycol, or a dialkyl carbonate and an alkanediol, wherein the alkylene glycol or the alkanediol obtained in the second step is recycled to the first step, the catalyst used in the first step is the same as the catalyst used in the second step, and a catalyst-containing reaction mixture obtained in the second step from which the dialkyl carbonate and unreacted alcohol are separated is recycled to the first step.

2. A process according to claim 1, wherein the first step is carried out under reduced pressure.

3. A process according to claim 1, wherein the first step is carried out in the presence of a catalyst formed of at least one member selected from the group consisting of zinc, magnesium, lead, calcium, a zinc compound, a magnesium compound, a lead compound and a calcium compound.

4. A process according to claim 1, wherein a reaction mixture containing the catalyst, obtained in the first step, is used as raw material and the catalyst in the second step.

5. A process according to claim 1, wherein unreacted alkylene glycol or unreacted alkanediol is separated from a reaction mixture containing the catalyst, obtained in the first step, and the remaining reaction mixture is used as raw materials and the catalyst in the second step.

6. A process according to claim 5, wherein the separated unreacted alkylene glycol or the separated unreacted alkanediol is recycled to the first step.

7. A process according to claim 1, wherein unreacted alkylene carbonate or unreacted six-membered cyclic carbonate separated from a reaction mixture obtained in the second step, is used as part of raw materials in the second step.

8. A process according to claim 1, wherein the catalyst separated from a reaction mixture obtained in the second step is used in the first step.

9. A process according to claim 1, wherein part of the catalyst separated from a reaction mixture obtained in the second step is used as the catalyst in the second step.

10. A process according to claim 9, wherein a remaining part of the catalyst separated from a reaction mixture obtained in the second step is used as the catalyst in the first step.

* * * * *